US012758570B2

(12) United States Patent
Bamat et al.

(10) Patent No.: US 12,758,570 B2
(45) Date of Patent: Oct. 13, 2026

(54) URIDINE TRIACETATE AMORPHOUS FORMULATION

(71) Applicant: PHARMA CINQ, LLC, Rockville, MD (US)

(72) Inventors: Michael Kevin Bamat, Potomac, MD (US); Yi Gao, Vernon Hills, IL (US); Jeffrey A. Miller, Lincoln University, PA (US); Yihong Qiu, Vernon Hills, IL (US)

(73) Assignee: PHARMA CINQ, LLC, Rockville, MD (US)

( * ) Notice: Subject to any disclaimer, the term of this patent is extended or adjusted under 35 U.S.C. 154(b) by 110 days.

(21) Appl. No.: 18/547,777

(22) PCT Filed: Jan. 27, 2022

(86) PCT No.: PCT/US2022/014031
§ 371 (c)(1),
(2) Date: Aug. 24, 2023

(87) PCT Pub. No.: WO2022/164985
PCT Pub. Date: Aug. 4, 2022

(65) Prior Publication Data

US 2024/0299434 A1 Sep. 12, 2024

Related U.S. Application Data

(60) Provisional application No. 63/142,297, filed on Jan. 27, 2021.

(51) Int. Cl.
*A61K 31/7072* (2006.01)
*A61K 47/32* (2006.01)
*A61K 47/38* (2006.01)

(52) U.S. Cl.
CPC .......... *A61K 31/7072* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 7,915,233 | B1 | 3/2011 | Von Borstel | |
| 2007/0259033 | A1* | 11/2007 | Cruz ...................... | A61K 31/00 424/452 |
| 2017/0000764 | A1 | 1/2017 | Lomuscio et al. | |
| 2018/0116911 | A1 | 5/2018 | Li | |
| 2019/0336487 | A1 | 11/2019 | Gu | |

FOREIGN PATENT DOCUMENTS

| | | | |
|---|---|---|---|
| CN | 101612110 | A * | 12/2009 |
| CN | 107753490 | A | 3/2018 |
| WO | 2018/115888 | A1 | 6/2018 |
| WO | 2020/226889 | A1 | 11/2020 |
| WO | 2022/164985 | A1 | 8/2022 |
| WO | 2024/025609 | A1 | 2/2024 |

OTHER PUBLICATIONS

Tanno et al. (Evaluation of Hypromellose Acetate Succinate (HPMCAS) as a carrier in solid dispersions, Drug Development and Industrial Pharmacy, vol. 30, No. 1, pp. 9-17, 2004) (Year: 2004).*
Chen et al., "Hypromellose Acetate Succinate," in *Handbook of Pharmaceutical Excipients*, pp. 350-353. London: Pharmaceutical Press. Jan. 1, 2006.
Tanno et al., "Evaluation of Hypromellose Acetate Succinate (HPMCAS) as a Carrier in Solid Dispersions," *Drug Development and Industrial Pharmacy* 30(1): 9-17 (2004).
International Search Report issued in International Application No. PCT/US22/14031, dated Apr. 12, 2022.
International Search Report issued in International Application No. PCT/US23/00027, dated Nov. 20, 2023.
Fukasawa et al., "Molecular weight determination of hypromellose acetate succinate (HPMCAS) using size exclusion chromatography with a multi-angle laser light scattering detector," *Chemical and Pharmaceutical Bulletin* 52(11): 1391-1393 (2004).
Millipore Sigma, "Improving API Solubility Using Hot Melt Extrusion Formulation With Polyvinyl Alcohol." Accessed May 15, 2026, at https://www.sigmaaldrich.com/US/en/technical-documents/technical-article/pharmaceutical-and-biopharmaceutical-manufacturing/solid-formulation-strategies/api-solubility-hot-melt-extrusion-polyvinyl-alcohol.
Sarabu et al., "Hypromellose acetate succinate based amorphous solid dispersions via hot melt extrusion: Effect of drug physicochemical properties," *Carbohydrate Polymers* 233: 115828 (2020).

* cited by examiner

*Primary Examiner* — Melissa S Mercier
(74) *Attorney, Agent, or Firm* — MEDLER FERRO WOODHOUSE & MILLS PLLC

(57) ABSTRACT

There is disclosed a dispersion of amorphous uridine triacetate in Hypromellose Acetate Succinate-MG and optionally also Copovidone. The amorphous dispersion compositions allow high loading of uridine. They also have good stability and oral bioavailability.

20 Claims, No Drawings

URIDINE TRIACETATE AMORPHOUS FORMULATION

BACKGROUND OF THE INVENTION

The pyrimidine nucleoside uridine has several potential clinical applications, including treatment of fluoropyrimidine toxicity and mitochondrial energy failure disorders. A barrier to therapeutic use of uridine is poor oral bioavailability, which has been measured at approximately 7% in both humans and mice. Uridine triacetate, an ester prodrug of uridine, in its crystalline form, improves oral bioavailability to approximately 50%. However, because relatively large doses of uridine triacetate are required for its therapeutic use in some disorders, up to 5 to 10 grams per dose, further improvement in bioavailability is important, both for reducing the amount of drug needed (and corresponding costs), and especially for therapeutic indications that benefit from a high peak concentration (Cmax) of plasma uridine, such as mitochondrial diseases and other energy failure disorders including but not limited to Huntington's Disease, Down Syndrome Dementia, age-related dementia and neuromuscular degeneration (sarcopenia), and vulnerability to secondary injury after acute brain injury such as traumatic brain injury, concussions, ischemic or hemorrhagic strokes, and asphyxia.

One important factor regulating the rate and extent of delivery of plasma uridine after oral administration of uridine triacetate is the rate of dissolution of crystals of this compound. Uridine triacetate has limited solubility in water, approximately 10 milligrams per milliliter.

Because relatively large doses of uridine triacetate are required, a high ratio of uridine triacetate to formulation excipients is important; however, a high ratio of uridine triacetate to excipients may result in poor stability, including crystal formation over time, creating both functional and regulatory problems. Furthermore, excipients must be safe in quantities compatible with the requisite amounts of uridine triacetate.

SUMMARY OF THE INVENTION

This invention provides a composition comprising amorphous uridine triacetate dispersed in one or more excipients, wherein the amount of the amorphous uridine triacetate is from about fifty to about sixty percent by weight of the composition; one of the one or more excipients is Hypromellose Acetate Succinate-M; and the amount of the Hypromellose Acetate Succinate-M is from about thirty-seven to about forty percent by weight of the composition.

DETAILED DESCRIPTION OF THE INVENTION

In an embodiment of the composition according to this invention, one of the one or more excipients is Copovidone. When the composition comprises Copovidone it is convenient for the amount of Copovidone to be about twelve percent by weight of the composition, for example about 12.5 percent by weight.

In a preferred embodiment of the composition according to this invention, the amount of amorphous uridine triacetate is about sixty percent by weight of the composition and the amount of the Hypromellose Acetate Succinate-M is about forty percent by weight of the composition. In another preferred embodiment the amount of amorphous uridine triacetate is about fifty percent by weight of the composition, and the one or more excipients comprise Hypromellose Acetate Succinate-M in an amount of about 37.5 percent by weight of the composition and Copovidone in an amount of about 12.5 percent by weight of the composition.

The amorphous dispersion compositions according to this invention allow high loading of uridine triacetate, adequate stability during storage, and improved oral bioavailability in comparison to equimolar doses of crystalline uridine triacetate particles. Moreover the compositions in accordance with this invention have improved taste and texture compared to the coated granules of crystalline uridine triacetate currently being commercialized. The compositions in accordance with this invention can optionally be mixed with soft foods such as applesauce, pudding or yogurt up to about thirty minutes before being ingested.

Generally, amorphous formulations are used when the active pharmaceutical ingredient (API) is very sparingly soluble and thus small amounts of API are made more soluble and thus bioavailable. It is not generally used with APIs, such as uridine triacetate, that are moderately soluble. An amorphous formulation of uridine triacetate allows practical oral delivery of a large amount of API. In the expressions "amorphous formulation" and "amorphous dispersion" of uridine triacetate, the term "amorphous" refers to the fact of the uridine triacetate being non-crystalline.

Amorphous dispersions are produced by one of two basic methods, spray drying or hot melt extrusion. In spray drying, the drug and excipients (generally including a polymer) are dissolved in a volatile solvent. The solution is sprayed as a fine mist and solvent is evaporated by heat or vacuum, leaving fine particles that are collected. In hot melt extrusion, the drug and excipients are melted together, mixed, extruded and cooled, yielding a solid material that can be milled to form particles of suitable size. In accordance with this invention the particles can be milled to any conventional size. For example it is convenient for the particles to have a D50 of about 200 microns.

Amorphous dispersion particles are optionally further formulated into aggregates, coated with taste masking or modified release excipients. Particles can also be incorporated into suspensions, capsules or tablets, including miniature tablets that are small enough to pass through gastrostomy or nasogastric tubes, or to be administered via an oral dosing syringe.

Uridine triacetate readily crystallizes under aqueous conditions. Therefore it was unexpected that hot melt extrusion compositions, such as formulation 1 (60% API/40% HPMCAS-M) and formulation 2 (50% API/37.5% HPMCAS-M/12.5% Copovidione), could be made successfully, display stability and overcome the challenge of targeting a very high drug load (≥50% uridine triacetate) of an API prone to reverting to a crystallized form, especially in the presence of moisture.

In the field of hot melt extrusion it is common to add a surfactant or plasticizer.

Nevertheless it was found that the hot melt extrusion of the formulations according to this invention did not require addition of a surfactant or plasticizer (Example 1 and Example 2). Without wishing to be bound by theory, it appears that uridine triacetate itself may be acting as a plasticizer.

Abbreviations and Definitions

HPMCAS means Hypromellose Acetate Succinate (a/k/a Hydroxypropyl Methyl Cellulose Acetate Succinate).

KF refers to the Karl Fischer method for the determination of moisture content.

RH means Relative Humidity.

Uridine triacetate is also known as 2',3',5'-Tri-O-acetyluridine or triacetyluridine.

The invention will be better understood by reference to the following examples, which illustrate but do not limit the invention described herein.

EXAMPLES

Example 1: Amorphous Solid Dispersion Consisting of 60% Uridine Triacetate and 40% Hypromellose Acetate Succinate-MG An amorphous solid dispersion (ASD) consisting of 60% Uridine Triacetate (w/w) active pharmaceutical ingredient (API) and 40% Hypromellose Acetate Succinate-M (HPMCAS-M) polymer was prepared by mixing Uridine Triacetate with Hydroxypropyl Methyl Cellulose Acetate Succinate-MG in ratios as described in Table 1, followed by hot melt extrusion with a twin screw extruder. The cooled extrusion was milled to a D50 of approximately 200 microns.

TABLE 1

Materials for 40% Uridine Triacetate and 60% Polymer Amorphous Solid Dispersion

| Chemical Name | Trade Name | % of Formulation | Source |
|---|---|---|---|
| Uridine Triacetate | NA | 60% | Wellstat |
| Hypromellose Acetate Succinate-MG | AquaSolve ™ HPMCAS-MG | 40% | Ashland |

Example 2: Amorphous Solid Dispersion Consisting of 50% Uridine Triacetate and 37.5% Hypromellose Acetate Succinate-MG and 12.5% Copovidone An amorphous solid dispersion (ASD) consisting of 50% Uridine Triacetate (w/w) active pharmaceutical ingredient (API), 37.5% Hypromellose Acetate Succinate-M (HPMCAS-M) and 12.5% Copovidone was prepared by mixing Uridine Triacetate with Hypromellose Acetate Succinate-MG and Copovidone polymers in the ratios as described in Table 2, followed by hot melt extrusion with a twin screw extruder. The cooled extrusion was milled to a D50 of approximately 200 microns.

TABLE 2

Materials for 60% Uridine Triacetate and 40% Polymer Amorphous Solid Dispersion

| Chemical Name | Trade Name | % of Formulation | Source |
|---|---|---|---|
| Uridine Triacetate | NA | 50% | Wellstat |
| Hypromellose Acetate Succinate-MG | AquaSolve ™ HPMCAS-MG | 37.5% | Ashland |
| Poly(1-vinylpyrrolidone-co-Vinyl Acetate) | Copovidone 35 M3 H. EUR./NF Type K28 | 12.5% | BASF |

Example 3: Stability of ASD Formulations 1 and 2 Under Long Term (25° C./60% RH) and Accelerated (40° C./75% RH) Conditions Formulation 1 (60% API) was stable for 12 weeks under long term (Table 3:25° C./60% RH) and accelerated conditions (Table 4:40° C./75% RH) with no increase in impurities or crystallinity as detected by HPLC and light microscopy, respectively.

Formulation 2 (50% API) was stable for 12 weeks under long term (Table 5:25° C./60% RH) and accelerated conditions (Table 6:40° C./75% RH) with no increase in impurities or crystallinity as detected by HPLC and light microscopy, respectively.

TABLE 3

Formulation 1 (60% API): 25° C./60% RH Stability

| Test | Initial | 4 Weeks | 6 Weeks | 12 Weeks |
|---|---|---|---|---|
| Appearance and Color | Off-white granules | Off-white granules | Off-white granules | Off-white granules |
| Assay | 100.9% | 98.3% | 99.9% | 100.1% |
| Impurities | | | | |
| Uridine | ND | ND | ND | ND |
| 2'5' diacetyluridine | <0.03% (0.02%) | 0.04% | <0.03% | 0.03% |
| 2'-acetyluridine + 3'-acetyluridine | ND | ND | ND | ND |
| 5'-acetyluridine | ND | ND | ND | ND |
| 2',3'-diacetyluridine | 0.04% | 0.08% | 0.03% | 0.06% |
| 2',5'-diacetyluridine + 3',5'-diacetyluridine | 0.05% | 0.10% | <0.03% | 0.07% |
| Individual Unknown Impurity | ND | ND | ND | ND |
| Total Impurities | 0.09% | 0.22% | 0.03% | 0.16% |

TABLE 3-continued

| Formulation 1 (60% API): 25° C./60% RH Stability | | | | |
|---|---|---|---|---|
| Test | Initial | 4 Weeks | 6 Weeks | 12 Weeks |
| Crystallinity | No Crystallinity Detected | No Crystallinity Detected | No Crystallinity Detected | No Crystallinity Detected |
| Moisture by KF | 0.73% | 0.61% | 0.56% | |

TABLE 4

| Formulation 1 (60% API): 40° C./75% RH Stability | | | | |
|---|---|---|---|---|
| Test | Initial | 4 Weeks | 6 Weeks | 12 Weeks |
| Appearance and Color | Off-white granules | Off-white granules | Off-white granules | Off-white granules |
| Assay | 100.9% | 98.4% | 100.3% | 100.0% |
| Impurities | | | | |
| Uridine | ND | ND | ND | ND |
| 2',5'-diacetyluridine | <0.03% (0.02%) | 0.04% | 0.03% | 0.06% |
| 2'-acetyluridine + 3'-acetyluridine | ND | ND | ND | ND |
| 5'-acetyluridine | ND | ND | ND | ND |
| 2',3'-diacetyluridine | 0.04% | 0.09% | 0.05% | 0.14% |
| 2',5'-diacetyluridine + 3',5'-diacetyluridine | 0.05% | 0.10% | 0.07% | 0.16% |
| Individual Unknown Impurity | ND | ND | ND | ND |
| Total Impurities | 0.09% | 0.232% | 0.15% | 0.36% |
| Crystallinity | No Crystallinity Detected | No Crystallinity Detected | No Crystallinity Detected | No Crystallinity Detected |
| Moisture by KF | 0.73% | 0.60% | 0.56% | |

TABLE 5

| Formulation 2 (50% API): 25° C./60% RH Stability | | | | |
|---|---|---|---|---|
| Test | Initial | 4 Weeks | 6 Weeks | 12 Weeks |
| Appearance and Color | Off-white granules | Off-white granules | Off-white granules | Off-white granules |
| Assay | 100.5% | 98.9% | 100.9% | 100.2% |
| Impurities | | | | |
| Uridine | ND | ND | ND | ND |
| 2',5'-diacetyluridine | 0.03% | 0.04% | <0.03% | 0.04% |
| 2'-acetyluridine + 3'-acetyluridine | ND | ND | ND | ND |
| 5'-acetyluridine | ND | ND | ND | ND |
| 2',3'-diacetyluridine | 0.05% | 0.07% | 0.03% | 0.07% |
| 2',5'-diacetyluridine + 3',5'-diacetyluridine | 0.07% | 0.09% | <0.03% | 0.09% |
| Individual Unknown Impurity | ND | ND | ND | ND |
| Total Impurities | 0.15% | 0.20% | 0.03% | 0.20% |
| Crystallinity | No Crystallinity Detected | No Crystallinity Detected | No Crystallinity Detected | No Crystallinity Detected |
| Moisture by KF | 0.88% | 0.78% | 0.76% | |

TABLE 6

| Formulation 2 (50% API): 40° C./75% RH Stability | | | | |
|---|---|---|---|---|
| Test | Initial | 4 Weeks | 6 Weeks | 12 Weeks |
| Appearance and Color | Off-white granules | Off-white granules | Off-white granules | Off-white granules |
| Assay | 100.5% | 98.8% | 100.5% | 100.8% |
| Impurities | | | | |
| Uridine | ND | ND | ND | ND |
| 2',5'-diacetyluridine | 0.03% | 0.05% | 0.03% | 0.08% |
| 2'-acetyluridine + 3'-acetyluridine | ND | ND | ND | ND |
| 5'-acetyluridine | ND | ND | ND | ND |
| 2',3'-diacetyluridine | 0.05% | 0.11% | 0.06% | 0.20% |
| 2',5'-diacetyluridine + 3',5'-diacetyluridine | 0.07% | 0.13% | 0.07% | 0.22% |
| Individual Unknown Impurity | ND | ND | ND | ND |
| Total Impurities | 0.15% | 0.28% | 0.16% | 0.50% |
| Crystallinity | No Crystallinity Detected | No Crystallinity Detected | No Crystallinity Detected | No Crystallinity Detected |
| Moisture by KF | 0.88% | 0.82% | 0.80% | |

What is claimed is:

1. A composition comprising amorphous uridine triacetate dispersed in one or more excipients, wherein the amount of the amorphous uridine triacetate is from about 50 to about 60% by weight of the composition;

the one or more excipients comprise Hypromellose Acetate Succinate-M; and the amount of the Hypromellose Acetate Succinate-M is from about 37 to about 40% by weight of the composition.

2. The composition of claim 1, wherein the one or more excipients comprise Hypromellose Acetate Succinate-M and Copovidone.

3. The composition of claim 2, wherein the amount of Copovidone is about 12% by weight of the composition.

4. The composition of claim 1, wherein the amount of amorphous uridine triacetate is about 60% by weight of the composition and the amount of the Hypromellose Acetate Succinate-M is about 40% by weight of the composition.

5. The composition of claim 2, wherein the amount of amorphous uridine triacetate is about 50% by weight of the composition, and the one or more excipients comprise Hypromellose Acetate Succinate-M in an amount of about 37.5% by weight of the composition and Copovidone in an amount of about 12.5% by weight of the composition.

6. The composition of claim 1, produced by hot melt extrusion.

7. The composition of claim 6, wherein the composition comprises particles having a D50 of about 200 microns.

8. The composition of claim 1, wherein the composition does not comprise a plasticizer other than the amorphous uridine triacetate.

9. The composition of claim 2, produced by hot melt extrusion.

10. The composition of claim 9, wherein the composition comprises particles having a D50 of about 200 microns.

11. The composition of claim 2, wherein the composition does not comprise a plasticizer other than the amorphous uridine triacetate.

12. The composition of claim 3, produced by hot melt extrusion.

13. The composition of claim 12, wherein the composition comprises particles having a D50 of about 200 microns.

14. The composition of claim 3, wherein the composition does not comprise a plasticizer other than the amorphous uridine triacetate.

15. The composition of claim 4, produced by hot melt extrusion.

16. The composition of claim 15, wherein the composition comprises particles having a D50 of about 200 microns.

17. The composition of claim 4, wherein the composition does not comprise a plasticizer other than the amorphous uridine triacetate.

18. The composition of claim 5, produced by hot melt extrusion.

19. The composition of claim 18, wherein the composition comprises particles having a D50 of about 200 microns.

20. The composition of claim 5, wherein the composition does not comprise a plasticizer other than the amorphous uridine triacetate.

* * * * *